United States Patent [19]

Akashiba et al.

[11] 4,363,875

[45] Dec. 14, 1982

[54] PROCESS FOR PRODUCING L-TRYPTOPHAN, AND A PURE CULTURE OF A MICROORGANISM STRAIN USED IN SAID PROCESS

[75] Inventors: Takeo Akashiba, Musashino; Akira Nakayama, Kawasaki; Atsuhiko Murata, Tokyo, all of Japan

[73] Assignee: Showa Denko K.K., Tokyo, Japan

[21] Appl. No.: 271,925

[22] Filed: Jun. 9, 1981

[30] Foreign Application Priority Data

Jun. 10, 1980 [JP] Japan ................................. 55/77130

[51] Int. Cl.$^3$ ..................... C12P 13/22; C12N 1/20; C12R 1/125
[52] U.S. Cl. .................................. 435/108; 435/253; 435/839
[58] Field of Search ............................. 435/108, 253

[56] References Cited

U.S. PATENT DOCUMENTS

| 3,700,558 | 10/1972 | Thiemann et al. | 435/108 |
| 3,700,559 | 10/1972 | Shiio et al. | 435/108 |
| 3,801,457 | 4/1974 | Arima et al. | 435/108 |
| 3,849,251 | 11/1974 | Nakayama et al. | 435/108 |

OTHER PUBLICATIONS

Bazzicalupo et al., Chemical Abstracts, vol. 92, 143110w (1980).

*Primary Examiner*—Lionel M. Shapiro
*Attorney, Agent, or Firm*—Wenderoth, Lind & Ponack

[57] ABSTRACT

In a process for producing L-tryptophan which comprises cultivating an L-tryptophan-producing mutant of *Bacillus subtilis* under aerobic conditions in a nutrient culture medium containing anthranilic acid, a carbon source, a nitrogen source and a mineral source, and recovering the resultant L-tryptophan from the culture broth, the improvement wherein the mutant is a strain resistant to 5-fluorotryptophan and 8-azaguanine; and a pure culture of a microorganism strain used in said process.

6 Claims, No Drawings

PROCESS FOR PRODUCING L-TRYPTOPHAN, AND A PURE CULTURE OF A MICROORGANISM STRAIN USED IN SAID PROCESS

This invention relates to an improved process for producing L-tryptophan by a fermentation technique which can give L-tryptophan in an increased yield; and to a pure culture of a novel microorganism strain for use in said process.

More specifically, this invention provides a process for producing L-tryptophan which comprises cultivating an L-tryptophan-producing mutant of *Bacillus subtilis* under aerobic conditions in a nutrient culture medium containing anthranilic acid, a carbon source, a nitrogen source and a mineral source, and recovering the resultant L-tryptophan from the culture broth, characterized in that the mutant is a strain resistant to 5-fluorotryptophan and 8-azaguanine.

It has been known that *Bacillus subtilis* has the ability to produce L-tryptophan (see, for example, U.S. Pat. Nos. 3,801,457 and 3,700,558). Its ability, however, is relatively low. In an attempt to improve this, many proposals have been made such as the use of various L-tryptophan-producing mutants of *Bacillus subtilis*, or the addition of a precursor to the nutrient culture medium. For example, Japanese Laid-Open Patent Publication No. 20391/1974 discloses a process for producing L-tryptophan which comprises cultivating an L-tryptophan-producing mutant of *Bacillus subtilis* in a nutrient culture medium containing anthranilic acid, a carbon source, a nitrogen source and a mineral source, and recovering the resultant L-tryptophan from the culture broth, wherein the mutant is a strain resistant to 5-fluorotryptophan, such as *Bacillus subtilis* SD-9 strain (FERM-P No. 1483; Fermentation Research Institute, Agency of Industrial Science and Technology, Japan).

The present inventors have made investigations in order to provide a more improved process for producing L-tryptophan by fermentation. These investigations have led to the discovery that a strain resistant to 5-fluorotryptophan and 8-azaguanine, which is not described in the literature, can be obtained from *Bacillus subtilis*, and this novel mutant has the ability to produce L-tryptophan at an increased rate of L-tryptophan accumulation and in an increased yield based on the carbon source (carbohydrate) consumed.

It is an object of this invention therefore to provide an improved process for producing L-tryptophan by fermentation.

Another object of this invention is to provide a pure culture of a microorganism strain which is suitable for use in the aforesaid process.

The above and other objects and advantages of this invention will become more apparent from the following description.

The novel L-tryptophan-producing mutant of *Bacillus subtilis* used in this invention is a 5-fluorotryptophan and 8-azaguanine resistant strain which is derived from known and freely available stains of *Bacillus substilis*.

Examples of the above parent strain include *Bacillus subtilis* IAM-1026 (Institute of Applied Microbiology, Japan); *Bacillus subtilis* ATCC 9466 (American Type Culture Collection, U.S.A.), and the various strains, e.g. ATCC 4925, ATCC 6051 and ATCC 6633, which are described in Agriculture Handbook No. 427, The Genus Bacillus (Agricultural Research Service, U.S. Department of Agriculture, October 1973), pages 182–183.

*Bacillus subtilis* SD-10 strain which belongs to the 5-fluorotryptophan and 8-azaguanine resistant strain in this invention is deposited in Fermentation Research Institute, Agency of Industrial Science and Technology, Japan under accession number FERM BP-4 as an internationally deposited strain in accordance with the Budapest Treaty.

The 5-fluorotryptophan and 8-azaguanine resistant strain used in this invention can be easily derived from the above-exemplified known and freely available parent strain *Bacillus subtilis* by known artificial mutation-inducing methods, e.g. known methods using mutagens (i.e., mutation-inducing substances) or radiating rays such as ultraviolet ray and X-ray.

Thus, according to this invention, there is provided a process for producing a strain of *Bacillus subtilis* which is capable of producing L-tryptophan and is resistant to 5-fluorotryptophan and 8-azaguanine, said process comprising (i) subjecting *Bacillus subtilis* to an artificial mutation-inducing treatment, (ii) cultivating the treated strain in a culture medium containing 5-fluorotryptophan in an amount larger than the minimum growth inhibitory concentration of the strain, (iii) further cultivating the cultivated strain in a culture medium containing 8-azaguanine in an amount larger than the minimum growth inhibitory concentration of the strain, and (iv) recovering the resulting strain having an increased ability to produce L-tryptophan.

The steps (i) to (iv) in the above process can be repeated a number of times as required.

According to one embodiment of the above process, a parent strain, such as *Bacillus subtilis* IAM-1026, is subjected to an artificial mutation-inducing treatment, for example irradiation of a mutation-inducing dose of an artificial mutation-inducing ray such as ultraviolet ray and X-ray, or cultivation in a culture medium containing a mutation-inducing amount of a mutagen such as acridine orange or N-methyl-N'-nitro-N-nitrosoguanidine. The strain so treated is then cultivated in a culture medium containing 5-fluorotryptophan in an amount larger than the minimum growth inhibitory concentration (MIC) of the strain, and the grown colonies are collected. The L-tryptophan-producing abilities of the grown colonies are tested, and a colony of the strain having increased ability to produce L-tryptophan is selected. Usually, this cultivation is repeated several times to obtain a 5-fluorotryptophan resistant strain of *Bacillus subtilis* having an increased ability to produce L-tryptophan. The L-tryptophan-producing mutant of *Bacillus subtilis* which can be obtained in the aforesaid manner is known, and disclosed, for example, in Japanese Laid-Open Patent Publication No. 20391/1974 cited above. The mutant is deposited, for example, under FERM-P No. 1483 at Fermentation Research Institute, Agency of Industrial Science and Technology, Japan.

In order to obtain the mutant used in this invention which has the ability to produce L-tryptophan and is resistant to 5-fluorotryptophan and 8-azaguanine, the 5-fluorotryptophan-resistant strain obtained as above is cultivated in a culture medium containing 8-azaguanine in an amount larger than the MIC of the strain, and the grown colonies are collected. The L-tryptophan-producing abilities of the grown colonies are tested, and a colony of the strain having an increased ability to produce L-tryptophan is selected. Usually, by repeating this cultivation several times, a strain having an increased L-tryptophan-producing ability and being resistant to 5-fluorotryptophan and 8-azaguanine can be obtained.

The mutant used in this invention which can be easily obtained from *Bacillus subtilis* or the 5-fluorotryptophan-resistant strain of *Bacillus subtilis* is preferably resistant to at least about 5,000 ppm of 5-fluorotryptophan and at least about 1,000 ppm of 8-azaguanine.

The dose of the ultraviolet ray mentioned above is, for example about 300 to about 800 erg/mm$^2$, and the dose of X-ray is, for example, about 150,000 to about 200,000 roentgen. The amount of the mutagen is, for example, 0.1 to 0.5% by weight, and the treating time is within one hour, for example.

In the above embodiment, the cultivation may be carried out under aerobic conditions in the same culture medium and under the same temperature and pH conditions as described below with regard to the process of this invention for L-tryptophan production.

Thus, according to this invention, there can be provided a biologically pure culture of *Bacillus subtilis* SD-10 strain which has the characteristics identified as FERM BP-4 deposited under the Budapest Treaty and has the ability to produce l-tryptophan by fermentation in a nutrient culture medium composed of a carbon source, a nitrogen source and a mineral source under aerobic conditions.

The L-tryptophan-producing mutant used in this invention which is resistant to 5-fluorotryptophan and 8-azaguanine has substantially the same morphological properties as the parent strain or the 5-fluorotryptophan-resistant strain thereof, and differs only in that its L-tryptophan-producing ability shows a marked increase, and it requires anthranilic acid (vitamin L$_1$) for production of L-tryptophan.

Specifically, the morphological properties of the mutant used in this invention are described in the above-cited Agriculture Handbook No. 427, The Genus Bacillus, pages 182–183.

According to the process of this invention, the L-tryptophan-producing strain resistant to 5-fluorotryptophan and 8-azaguanine is cultivated under aerobic conditions in a culture medium containing anthranilic acid, a carbon source, a nitrogen source and a mineral source, and the resulting L-tryptophan is recovered from the culture broth.

The carbon source may be any carbon-containing materials which can be assimilated by the strain. Examples include carbohydrates such as glucose, molasses, sucrose, starch, saccharified starch solution and decomposition products of cellulose; organic acids such as acetic acid; and alcohols such as ethanol. Examples of the nitrogen source are ammonia, ammonium salts such as ammonium sulfate, ammonium chloride, ammonium nitrate and ammonium phosphate, urea, and nitrate salts. Examples of the mineral source include salts of P, Na, K, Mg, Fe, and Mn, for example inorganic salts such as ammonium phosphate, potassium phosphate, sodium phosphate, potassium sulfate, potassium hydroxide, magnesium sulfate, ferrous sulfate and manganese sulfate. Inorganic salts of Ca, Zn, B, Cu, Co, Mo, etc. may also be added as trace element components. Furthermore, as traces of organic nutrients, there may be added vitamins and amino acids, which are not particularly required for the growth of the strain, and other organic materials such as corn steep liquor, meat extract, yeast extract, and peptone.

Anthranilic acid may be added in the form of an aqueous solution of sodium, potassium or ammonium anthranilate or as a solution of free anthranilic acid in ethanol or acetone.

The cultivation is carried out under aerobic conditions by, for example, techniques of shaking culture, bubbling and stirring cultivation or other cultivation techniques under aerobic conditions.

The cultivation may be carried out at a temperature of 25° to 45° C. and a pH of 5 to 9, preferably 6 to 8. A suitable cultivation time can be selected, and is, for example, about 15 to about 60 hours.

The suitable concentration of anthranilic acid included in the nutrient culture medium is up to the minimum growth inhibitory concentration (MIC) of the strain, for example up to about 0.1% by weight, preferably 5 to 300 ppm, based on the weight of the culture medium. Preferably, the anthranilic acid is added at the early stage of cultivation. It is intermittently or continuously added to the cultivation medium so that its concentration in the cultivation medium does not exceed the minimum growth inhibitory concentration of the strain. Slightly higher concentrations of the anthranilic acid than the minimum growth inhibitory concentration of the strain do not so much affect the growth of the strain itself, but inhibit the production of L-tryptophan. Accordingly, anthranilic acid is preferably added intermittently or continuously according to the rate of its consumption in order to avoid its accumulation in the culture medium or a temporary increase of its concentration therein. In the absence of anthranilic acid in the culture medium, the above mutant strain in accordance with this invention shows a normal growth of cells, but accumulation of L-tryptophan is scarcely noted.

The resulting L-tryptophan is isolated in a customary manner from the culture broth after the cultivation. For example, the culture broth is sterilized at 80° C. for 30 minutes and centrifuged, followed by addition of an acid to decrease the pH of the supernatant liquid to 2 or below. It is then charged on a column of a strong acid-type cation exchange resin to cause adsorption of L-tryptophan. The column is washed with water and then eluted with dilute ammonia solution to separate L-tryptophan. The eluate is then stripped with ammonia under reduced pressure to collect crude crystals of the resulting L-tryptophan. The crude crystals are dissolved in 70% ethanol at an elevated temperature. A small amount of activated carbon is added, and the solution is hot-filtered. The filtrate is cooled and the resulting L-tryptophan crystals are collected by filtration.

The following examples illustrate the present invention more specifically.

EXAMPLE 1 AND COMPARATIVE EXAMPLE 1

Two liters of a liquids culture medium having the following composition, i.e.
glucose 10%,
ammonium sulfate 0.3%,
Na$_2$HPO$_4$.12H$_4$O 0.5%,
KH$_2$PO$_4$x.H$_2$O 0.2%,
MgSO$_4$.7H$_2$O 0.1%,
FeSO$_4$.7H$_2$O 0.5 mg%, and
MnSO$_4$.4–6H$_2$O 0.1 mg%,
was put in a 5-liter jar fermentor, and sterilized at 115° C. for 15 minutes. *Bacillus subtilis* SD-10 (FERM BP-4)

which had been cultivated with shaking at 30° C. for 12 hours in a nutrient medium was inoculated in an amount of 5% in the above fermentor, and cultivated at 35° C. with aeration by stirring while maintaining the amount of dissolved oxygen at 0.5 ppm or higher. A 5% aqueous solution of sodium anthranilate was continuously added so that its concentration in the culture medium was maintained below the minimum growth inhibitory concentration of the above microorganism strain. The cultivation was continued for 30 hours while maintaining the pH of the culture broth at 7.0. L-tryptophan was formed and accumulated in a concentration of 14.6 g/liter. The yield of L-tryptophan was 16.5% based on the consumed glucose, and 99 mole% based on the anthranilic acid.

For comparison, the above procedure was repeated except that the aqueous solution of sodium anthranilate was not used (Comparative Example 1). The amount of L-tryptophan formed and accumulated at the end of 30 hour's cultivation was 250 mg/liter.

EXAMPLE 2 AND COMPARATIVE EXAMPLE 2

*Bacillus subtilis* SD-10 was cultivated for 20 hours in the same culture medium as used in Example 1 in a 5-liter jar fermentor. Then, 750 ml of the resulting culture broth was inoculated in 15 liters of the same culture medium in a 30-liter jar fermentor, and cultivated at 35° C. with aeration by stirring while maintaining the amount of dissolved oxygen at 0.5 ppm or higher. A 10% aqueous solution of sodium anthranilate was added continuously so that the concentration of anthranilic acid in the culture medium was maintained below the minimum growth inhibitory concentration of the microorganism strain. The cultivation was continued for 24 hours while maintaining the pH of the culture broth at 7.0. Thus, L-tryptophan was formed and accumulated in a concentration of 15.6 g/liter. The yield of L-tryptophan was 17.4% based on the glucose consumed, and 99 mole% based on the anthranilic acid.

For comparison, the above procedure was repeated except that *Bacillus subtilis* SD-9 (FERM-P 1483; described in Japanese Laid-Open Patent Pubilcation No. 20391/1974) was used as the seed strain. L-tryptophan was formed and accumulated in a concentration of 4.8 g/liter. The yield of L-tryptophan was 5.2% based on the glucose consumed, and 92 mole% based on the anthranilic acid.

EXAMPLE 3

Production of a biologically pure culture of *Bacillus subtilis*

*Bacillus subtilis* IAM-1026 (Institute of Applied Microbiology) was subjected to ultraviolet radiation to derive an artificial mutant from the parent strain in a nutrient medium in a customary manner. The resulting mutant was incubated in a nutrient agar containing 5-fluorotryptophan. Several hundred colonies grown on the agar plate were tested for the ability to produce L-tryptophan by fermentation, and a colony of the strain having the best L-tryptophan-producing ability was selected. The selected strain was treated by the above-mentioned artificial mutating method, and the selection of a 5-fluorotryptophan-resistant mutant followed. The above treatment and selection were repeated several times to obtain a mutant being substantially resistant to up to 5,000 ppm of 5-fluorotryptophan.

Next, this 5-fluorotryptophan-resistant mutant was treated again by the same artificial mutating method as above, and the selection of an 8-azaguanine-resistant mutant followed in the same way as the selection of the 5-fluorotryptophan-resistant mutant. The final mutant was found to be resistant to up to 1,000 ppm of 8-azaguanine. It was also resistant to 5-fluorotryptophan.

What we claim is:

1. In a process for producing L-tryptophan which comprises cultivating an L-tryptophan-producing mutant of *Bacillus subtilis* under aerobic conditions in a nutrient culture medium containing anthranilic acid, a carbon source, a nitrogen source and a mineral source, and recovering the resultant L-tryptophan from the culture broth, the improvement wherein the mutant is a strain resistant to 5-fluorotryptophan and 8-azaguanine.

2. The process of claim 1 wherein the mutant is *Bacillus subtilis* SD-10 strain.

3. The process of claim 1 wherein the cultivation is carried out at a temperature of 25° to 45° C. and a pH of 5 to 9.

4. The process of claim 1 wherein the concentration of the anthranilic acid in the culture medium is up to the minimum growth inhibitory concentration of the strain.

5. The process of claim 4 wherein the concentration of the anthranilic acid is up to about 0.1% by weight based on the weight of the culture medium.

6. A biologically pure culture of *Bacillus subtilis* SD-10 strain which has the characteristics identified as FERM BP-4 deposited under the Budapest Treaty and has the ability to produce L-tryptophan by fermentation in a nutrient culture medium containing anthranilic acid, a carbon source, a nitrogen source and a mineral source under aerobic conditions.

* * * * *